US010642959B2

(12) United States Patent
Tutera

(10) Patent No.: US 10,642,959 B2
(45) Date of Patent: May 5, 2020

(54) SYSTEMS AND METHODS FOR CALCULATING PATIENT DOSAGE

(71) Applicant: THE SOTTOPELLE GROUP, LLC, Scottsdale, AZ (US)

(72) Inventor: Gino Tutera, Paradise Valley, AZ (US)

(73) Assignee: The SottoPelle Group, LLC, Scottsdale, AZ (US)

( * ) Notice: Subject to any disclaimer, the term of this patent is extended or adjusted under 35 U.S.C. 154(b) by 905 days.

(21) Appl. No.: 15/175,033

(22) Filed: Jun. 7, 2016

(65) Prior Publication Data

US 2016/0292387 A1  Oct. 6, 2016

Related U.S. Application Data

(63) Continuation of application No. 13/721,949, filed on Dec. 20, 2012, now abandoned, which is a
(Continued)

(51) Int. Cl.
*A61K 38/22* (2006.01)
*A61P 3/00* (2006.01)
*G06F 19/00* (2018.01)
*G06Q 50/22* (2018.01)
*G06Q 10/00* (2012.01)

(52) U.S. Cl.
CPC ......... *G06F 19/3456* (2013.01); *G06Q 10/00* (2013.01); *G06Q 50/22* (2013.01)

(58) Field of Classification Search
CPC ............ C12Q 1/6883; C12Q 2600/106; C12Q 2600/156; G01N 2333/575; G01N 2800/2835; G01N 33/6896; G01N 33/743; G01N 2800/52; A61K 2300/00; A61K 2039/505; A61K 2039/545; G06F 19/3456; G06F 19/324; G06F 19/328; G16H 20/10; G16H 50/20
See application file for complete search history.

(56) References Cited

U.S. PATENT DOCUMENTS

2010/0267767 A1  10/2010 Narayanan et al.
2011/0066450 A1   3/2011 Karapanos
(Continued)

OTHER PUBLICATIONS

Mason, Innovative Diagnostic and Treatment Options, Alternative & Complementary Therapies, Aug. 2007, 13(4):211-216.
(Continued)

*Primary Examiner* — Maroun P Kanaan
(74) *Attorney, Agent, or Firm* — Michelle L. Gross, P.C.

(57) ABSTRACT

Systems and methods for providing a dosage on a device comprising an electronic circuit, an input device, and a display screen. The method includes receiving an input signal of a user indicating an input directed to a patient sex and patient status selected from the group comprising new patient, returning patient and booster patient. If the patient sex is female, an effective estradiol dosage and an effective testosterone dosage are determined using dosage calculation methods selected based on the patient status and additional female input parameters. If the patient sex is male an effective testosterone dosage is determined using dosage calculation methods selected based on the patient status and additional male input parameters.

20 Claims, 5 Drawing Sheets

Related U.S. Application Data continuation of application No. 13/548,714, filed on Jul. 13, 2012, now abandoned.

(60) Provisional application No. 61/507,318, filed on Jul. 13, 2011.

(56) References Cited

U.S. PATENT DOCUMENTS

2011/0077226 A1\* 3/2011 Carnazza .............. A61K 31/56
 514/170
2011/0190201 A1 8/2011 Hyde et al.

OTHER PUBLICATIONS

Nelson, Implementing Metrics Management for Improving Clinical Trials Performance, originally published Jul. 17, 2008, in BeyeNETWORK, US Edition, available online at https://web.archve.org/web/20130510020333/http://www.b-eye-network.com/view/7981.
PCT International Search Report and Written Opinion, PCT/US2015/19963, dated Jun. 10, 2015, 15 pages.

\* cited by examiner

SYSTEMS AND METHODS FOR CALCULATING PATIENT DOSAGE

CROSS-REFERENCE TO RELATED APPLICATIONS

This application is a continuation of co-pending U.S. patent application Ser. No. 13/721,949, filed Dec. 20, 2012, which is a continuation of co-pending U.S. patent application Ser. No. 13/548,714, filed Jul. 13, 2012, which claims benefit of U.S. Provisional Patent Application No. 61/507,318, filed on Jul. 13, 2011, the disclosures of which are incorporated herein by reference in their entireties.

BACKGROUND

Field

Embodiments include systems and methods for determining the most effective and safe dosage for hormone replacement therapy.

Description of the Related Art

Hormone replacement therapy includes estradiol and testosterone for females and testosterone for males. Traditionally, determination of recommended dosage for hormone replacement therapy requires that a physician consider numerous factors, including patient age, weight/height, health conditions, contraindications, hormonal levels, previous and current medications, and the like. In all, a proper determination involves correct consideration and weighing of many factors, some of which the physician may not even have easy access to, such as a patient's detailed health record. Systems and methods for automating the determination of dosage for hormone replacement therapy which take into account the relevant factors and apply a consistent formulaic approach to minimize incorrect dosage determinations are desirable.

SUMMARY

Systems and methods for providing a dosage on a device comprising an electronic circuit, an input device, and a display screen are provided. The methods include receiving, from the input device, an input signal of a user indicating an input directed to a patient sex and patient status, wherein patient status is selected from the group including new patient, returning patient and booster patient. If the patient sex is female, the electronic circuit determines an effective estradiol dosage and an effective testosterone dosage using dosage calculation methods selected based on the patient status and additional female input parameters. If the patient sex is male, the electronic circuit determines an effective testosterone dosage using dosage calculation methods selected based on the patient status and additional male input parameters. The determined effective dosages may then be displayed on the display screen.

In an aspect of the invention, the additional female input parameters include age, height, weight, race, number of pregnancies, number of live births, number of abortions, history of renal disease, active liver disease, hysterectomy, history of cervical cancer, history of ovarian cancer, fibrocystic breast disease, history of breast cancer, current follicle stimulating hormone (FSH) level, current testosterone level, current estradiol level, current non-pellet estradiol dose, history of acne or facial hair, history of hair loss, history of PCOS, history of hysterectomy, history of heavy menses and history of metabolic syndrome.

In additional aspects, the dosage determination for a female new patient further includes the electronic circuit receiving patient age and weight, determining patient weight/age ratio, looking up predetermined dosage values based on weight/age estradiol, weight testosterone, age estradiol, testosterone level, follicle stimulating hormone (FSH) level, and a current dose. The electronic circuit then determines a problem factor adjustment and an FSH adjustment, wherein the FSH adjustment is 12.5 mg if the patient age is greater than or equal to 30 years. The electronic circuit next determines an estradiol dosage according to:

estradiol dosage=((weight/age estradiol ratio lookup+ age estradiol lookup+FSH lookup)×problem factor adjustment)+FSH adjustment and a testosterone dosage according to:

testosterone dosage=(weight testosterone ratio lookup+testosterone level lookup)×testosterone age lookup.

further aspect of the invention provides the problem factor adjustment as a value determined to be the multiplicative product of the one or more values selected from the group comprising:

1.00 for no problem adjustment,
0.90 for patient history of acne or facial hair,
0.88 for history of hair loss,
0.75 for history of PCOS,
0.88 for hysterectomy,
0.70 for history of fibrocystic breast disease,
0.88 for history of heavy menses,
0.80 for persistent breast pain,
0.80 for mid-cycle bleeding,
0.75 for headaches,
0.75 for fluid retention, and
0.00 for history of metabolic syndrome.

A further aspect provides a dosage determination method for a female returning patient further, in which the electronic circuit receives the patient age and weight, and determines the patient weight/age ratio. Next the electronic circuit looks up predetermined values in tables weight/age estradiol value, a weight testosterone value, an age estradiol value, a current estradiol dose value, a testosterone level value, a follicle stimulating hormone (FSH) value, and a current dose value. The electronic circuit may also determine a returning female problem factor adjustment such as:

1.00 for no problem adjustment,
0.90 for history of acne or facial hair,
0.88 for history of hair loss,
0.75 for history of PCOS,
0.88 for hysterectomy,
0.70 for history of fibrocystic breast disease,
0.88 for history of heavy menses,
0.80 for persistent breast pain,
0.80 for mid-cycle bleeding,
0.75 for headaches,
0.75 for fluid retention, and
0.00 for history of metabolic syndrome.

A further aspect provides a dosage determination method for a female returning patient further, in which the electronic circuit receives the patient age and weight, and determines the patient weight/age ratio. Next the electronic circuit looks up predetermined values in tables weight/age estradiol value, a weight testosterone value, an age estradiol value, a current estradiol dose value, a testosterone level value, a follicle stimulating hormone (FSH) value, and a current dose value. The electronic circuit may also determine a returning female problem factor adjustment such as:

1.00 for no problem adjustment,
0.90 for history of acne or facial hair,
0.88 for history of hair loss,
0.75 for history of PCOS,
0.88 for hysterectomy,
0.70 for history of fibrocystic breast disease,
0.88 for history of heavy menses,
0.80 for persistent breast pain,
0.80 for mid-cycle bleeding,
0.75 for headaches,
0.75 for fluid retention, and
0.00 for history of metabolic syndrome.

The electronic circuit then determines an estradiol dosage according to:

$$\text{estradiol dosage} = (\text{weight/age estradiol ratio lookup} + \text{age estradiol lookup} + \text{FSH lookup} + \text{current estradiol dose lookup}) \times \text{problem factor adjustment},$$

and, a testosterone dosage according to:

$$\text{testosterone dosage} = (\text{weight testosterone ratio lookup} + \text{testosterone level lookup}) \times \text{testosterone age lookup}.$$

In another aspect of the invention, the electronic circuit determines the dosage female booster patient by receiving information such as patient previous estradiol dosage, previous testosterone dosage, whether patient is pre-menopausal, estradiol level, and whether patient has migraines, and then, if patient is not pre-menopausal, or is pre-menopausal with estradiol level less than 10 or migraines, an estradiol dosage is determined according to:

$$\text{estradiol dosage} = \text{previous estradiol dosage}/2.00.$$

Otherwise, if the patient is pre-menopausal, estradiol is greater than or equal to 10 or patient has migraines, estradiol dosage=0. Also, testosterone dosage for a booster patient is determined according to:

$$\text{testosterone dosage} = \text{previous testosterone dosage}/3.00.$$

Also provided in an aspect of the invention, additional male input parameters for testosterone dosing include patient age, height, weight, race, history of hypertension, history of diabetes, history of colon cancer, history of testicular cancer, history of BPH, history of prostate cancer, history of renal disease, active liver disease, and current testosterone level. The electronic circuit receives patient age, height, weight, race, history of hypertension, history of diabetes, history of colon cancer, history of testicular cancer, history of BPH, history of prostate cancer, history of renal disease, active liver disease and current testosterone level, and then looks up predetermined values such as a weight lookup value, an age lookup value, and a current dose lookup value. Next, the electronic circuit determines an additional adjustment factor according to:
1.00 for no problem adjustment,
0.95 for history of BPH,
0.90 for history of prostate cancer,
0.90 for history of both prostate cancer and BPH, ignoring individual values for these conditions, and
0.00 if patient testosterone level greater than 700.

The electronic circuit then determines a male patient testosterone dosage according to:

$$\text{testosterone dosage} = \text{weight lookup value} \times \text{age lookup value} \times \text{additional adjustment}.$$

The determined testosterone dosage may then be modified as follows:

history of diabetes,dosage=dosage+100 mg, sedentary patient,dosage=dosage−100 mg;

patient exercises five times/week or more, dosage=dosage+100 mg, and patient uses a testosterone gel 1.62% or greater, dosage=dosage−100 mg.

For male return patients, if the current testosterone dosage is less than 400.00 mg, then the new dosage=previous testosterone dosage+200.00 mg, otherwise the new dosage remains the same as the previous dosage.

In addition, in another aspect of the invention, the electronic circuit determines the testosterone dosage for a male booster patient as follows:

$$\text{booster dosage} = \text{previous testosterone dosage} + 0.20 \text{ mg} \times \text{additional adjustment};$$

where additional adjustment is determined as the multiplicative product of the one or more values selected from the group including:

0.00 for no problem adjustment,
0.95 for history of BPH,
0.90 for history of prostate cancer,
0.90 for history of both prostate cancer and BPH, ignoring individual values for these conditions, and
0.00 if testosterone level greater than 700.

Also disclosed are devices including a non-transient computer readable medium incorporating computer instructions including the above-referenced methods.

BRIEF DESCRIPTION OF THE DRAWINGS

Embodiments will be described with reference to the following drawing figures, in which like numerals represent like items throughout the figures, and in which.

DETAILED DESCRIPTION

Figure 1:
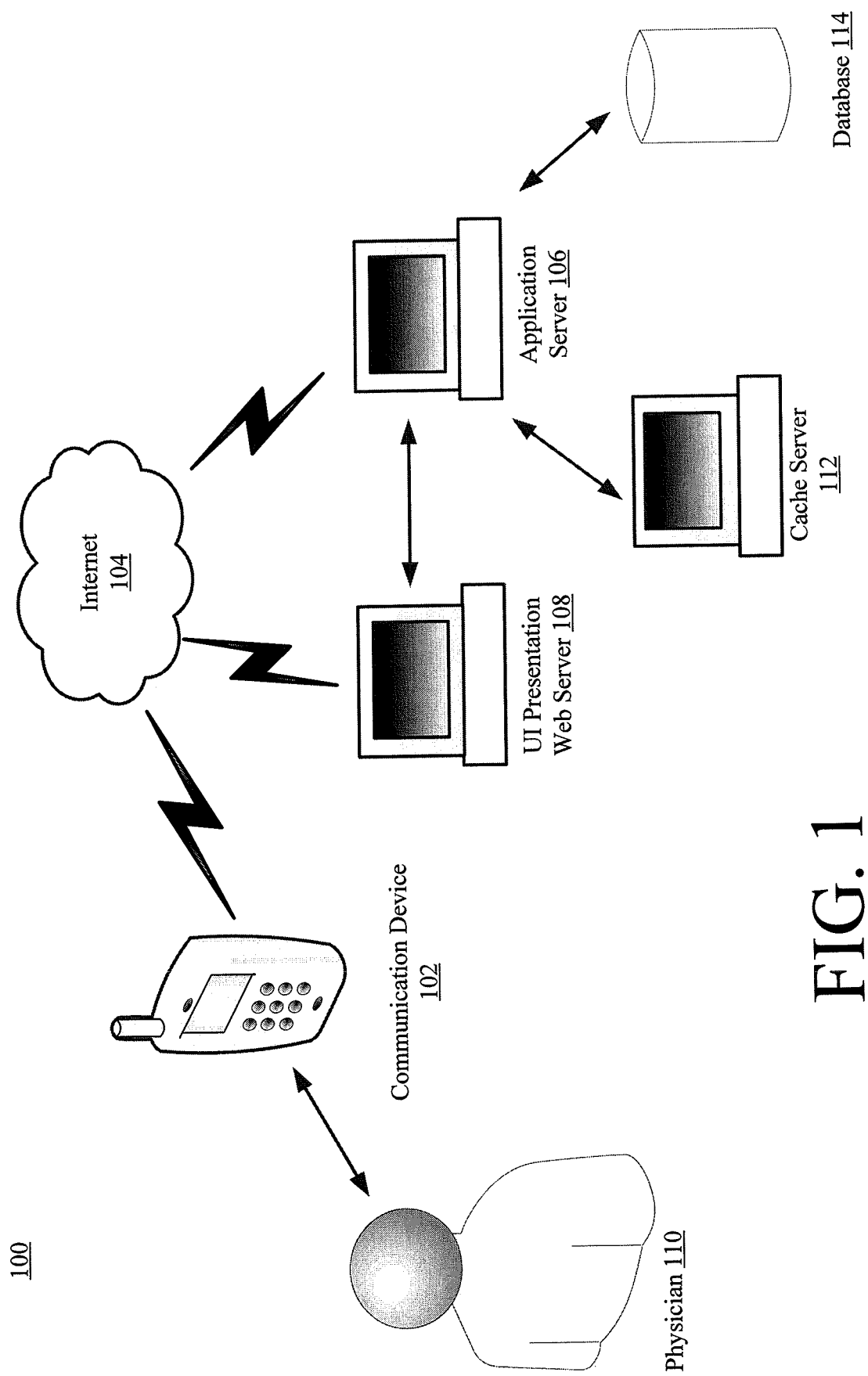
FIG. 1 is a schematic system diagram of an exemplary system that is useful for understanding the present invention.

The present invention is described with reference to the attached figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is if, X employs A; X employs B; or X employs both A and B, then "X employs A or B" is satisfied under any of the foregoing instances.

The present invention concerns implementing systems and methods for determining the most effective and safe dosage for hormone replacement therapy. While the specific implementations described herein are directed to determining dosage for hormone replacement therapy, it is envisioned that the systems and methods described herein can be used with minor modification for determining recommended dosage in other drug-related health areas, without limitation. SOTTOPELLE™ hormone replacement therapy ("HRT") using Hormone Pellet Therapy is a highly effective form of HRT. This treatment method is based on prescribing the right kind of hormone (e.g., biologically identical), in the correct amounts (e.g., determined through testing & proper analysis of the results), using the right delivery system (e.g., pellets).

A crucial element to effective HRT is determining and providing the proper dosage of hormones to the patient. Correct dosing requires processes that consider numerous factors, the proper mathematical weighting of those factors, as well as significant input from the patient history and other related elements. These processes, tables, factors and related items for calculation of proper dosages for SOTTOPELLE™ HRT are described herein.

The present invention provides a system and method for calculating HRT dosage, in particular for calculation of SOTTOPELLE™ HRT dosage. The processes, tables and factors and related items described herein are advantageously incorporated onto a system having at a minimum an electronic circuit and related electronic memory, as well as input/out devices controlled by the electronic circuit. The processor and memory are configured to interface with a user through the input/output devices to obtain the information needed to apply the processes, tables, factors and related items described herein and further configured to determine the correct dosage for SOTTOPELLE™ HRT. A database is also envisioned to be accessible by the electronic circuit and to store data regarding the patient, patient test results, prior dosing information, prior side effects, and any other medically significant information. The electronic circuit may then access the database for information and may also store information therein.

Although described in terms of various components used to implement the methods, the present invention can be used in a variety of system configurations, such as, but not limited to, mobile phone applications, portable computer applications, PDA applications, and the like. Also, various system components may be combined into a few or even one hardware component(s) without affecting overall functionality. Exemplary implementing system embodiments of the present invention will be described below in relation to FIGS. 2-3. Exemplary method embodiments of the present invention will be described below in relation to FIGS. 4-5.

Exemplary Systems Implementing the Present Invention

Referring now to FIG. 1, there is provided a block diagram of an exemplary system 100 that is useful for understanding various embodiments of the present invention. The system 100 comprises communication device 102, a network 104, a user interface (UI) presentation server 108, an application server 106, a cache server 112, and a database 114. Also depicted is a physician user 110, for illustrative purposes. The system 100 may include more, less or different components than those illustrated in FIG. 1. However, the components shown are sufficient to disclose an illustrative embodiment implementing the present invention. In particular, the functionality of the UI presentation server 108, application server 106, and cache server 112 may be combined into one or two servers in various embodiments without affecting the efficacy of the invention. Also, servers 106, 108 and 112 may include identical components or may differ in composition, and are described generically herein as "server 106, 108, 112".

In an embodiment, the UI presentation server provides the user interface to the communication device 102 over the Internet 104. Information input through the communication device 102 is forwarded to the application server 106 for processing and/or storage in the database 114. The cache server 112 saves frequently-used data for fast access as needed.

The database 114 component may be a stand-alone database server, a persistent drive and operating software associated with the application server 106, a cloud-computing database "cloud", or may be implemented by other means.

The communication device 102 is configured to communicate with a server 108 over a network 104 to send and obtain information regarding a patient. This information can include, but is not limited to, information needed for enabling the determination of recommended dosages for hormone replacement therapy.

Figure 2:
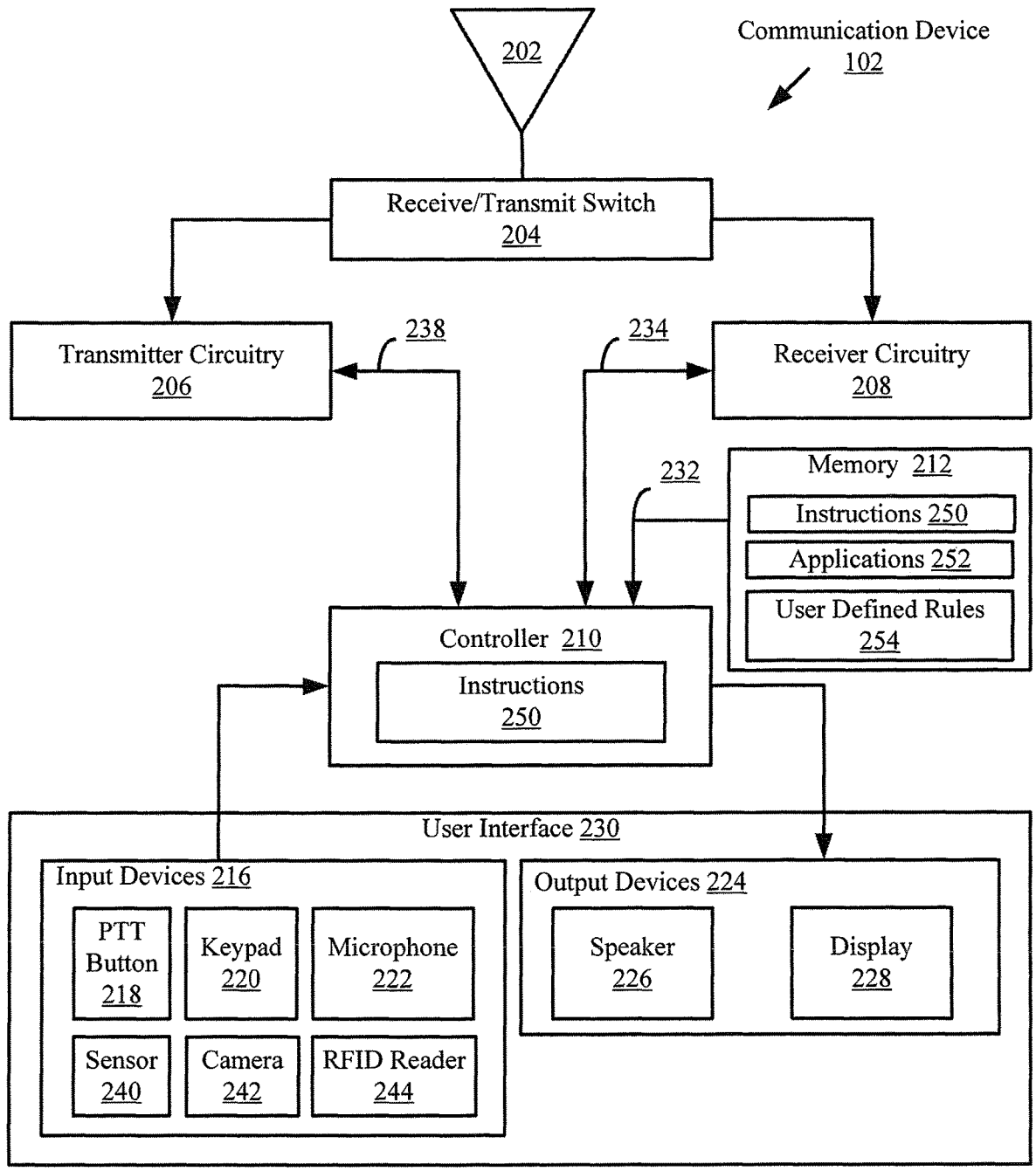
FIG. 2 is a block diagram of an exemplary communication device that is useful for understanding the present invention.

Referring now to FIG. 2, there is provided a more detailed block diagram of the communication device 102. The communication device 102 will be described herein as comprising a mobile phone or a smart phone. However, the present invention is not limited in this regard. For example, the communication device can alternatively comprise a PDA, a tablet Personal Computer ("PC"), or the like.

Notably, the communication device 102 can include more or less components than those shown in FIG. 2. For example, the communication device 102 can include a wired system interface, such as a universal serial bus interface (not shown in FIG. 2). However, the components shown are sufficient to disclose an illustrative embodiment implementing the present invention.

As shown in FIG. 2, the communication device 102 comprises an antenna 202 for receiving and transmitting Radio Frequency (RF) signals. A receive/transmit (Rx/Tx) switch 204 selectively couples the antenna 202 to the transmitter circuitry 206 and receiver circuitry 208 in a manner familiar to those skilled in the art. The receiver circuitry 208 demodulates and decodes the RF signals received from a network (e.g., the network 104 of FIG. 1) to derive information therefrom. The receiver circuitry 208 is coupled to a controller 210 via an electrical connection 234. The receiver circuitry 208 provides the decoded RF signal information to the controller 210. The controller 210 uses the decoded RF signal information in accordance with the function(s) of the communication device 102. The controller 210 also provides information to the transmitter circuitry 206 for encoding and modulating information into RF signals. Accordingly, the controller 210 is coupled to the transmitter circuitry 206 via an electrical connection 238. The transmitter circuitry 206 communicates the RF signals to the antenna 202 for transmission to an external device (e.g., network equipment of network 104 of FIG. 1).

The controller 210 stores the decoded RF signal information in a memory 212 of the communication device 102. Accordingly, the memory 212 is connected to and accessible by the controller 210 through an electrical connection 232. The memory 212 can be a volatile memory and/or a non-volatile memory. For example, the memory 212 can include, but is not limited to, a Random Access Memory (RAM), a Dynamic Random Access Memory (DRAM), a Static Random Access Memory (SRAM), Read-Only Memory (ROM) and flash memory. The memory 212 can also have stored therein the software applications 252 and user-defined rules 254.

The software applications 252 may include, but are not limited to, applications operative to provide telephone services, network communication services, Internet connectivity and access services, commerce services, email services, web based services, and/or electronic calendar services.

As shown in FIG. 2, one or more sets of instructions 250 are stored in the memory 212. The instructions 250 can also reside, completely or at least partially, within the controller 210 during execution thereof by the communication device 102. In this regard, the memory 212 and the controller 210 can constitute non-transient machine-readable media. The term "machinereadable media", as used here, refers to a single medium or multiple media that store the one or more sets of instructions 250. The term "machine-readable media", as used here, also refers to any medium that is capable of storing, encoding or carrying the set of instructions 250 for execution by the communication device 102 and that cause the communication device 102 to perform one or more of the methodologies of the present disclosure.

The controller 210 is also connected to a user interface 230. The user interface 230 is comprised of input devices 216, output devices 224, and software routines (not shown in FIG. 5) configured to allow a user to interact with and control software applications 252 installed on the computing device 102. Such input and output devices respectively include, but are not limited to, a display 228, a speaker 226, a keypad 220, a directional pad (not shown in FIG. 5), a directional knob (not shown in FIG. 2), a microphone 222, a Push-To-Talk ("PTT") button 218, sensors 240, a camera 242 and a Radio Frequency Identification ("RFID") reader 244.

Figure 3:
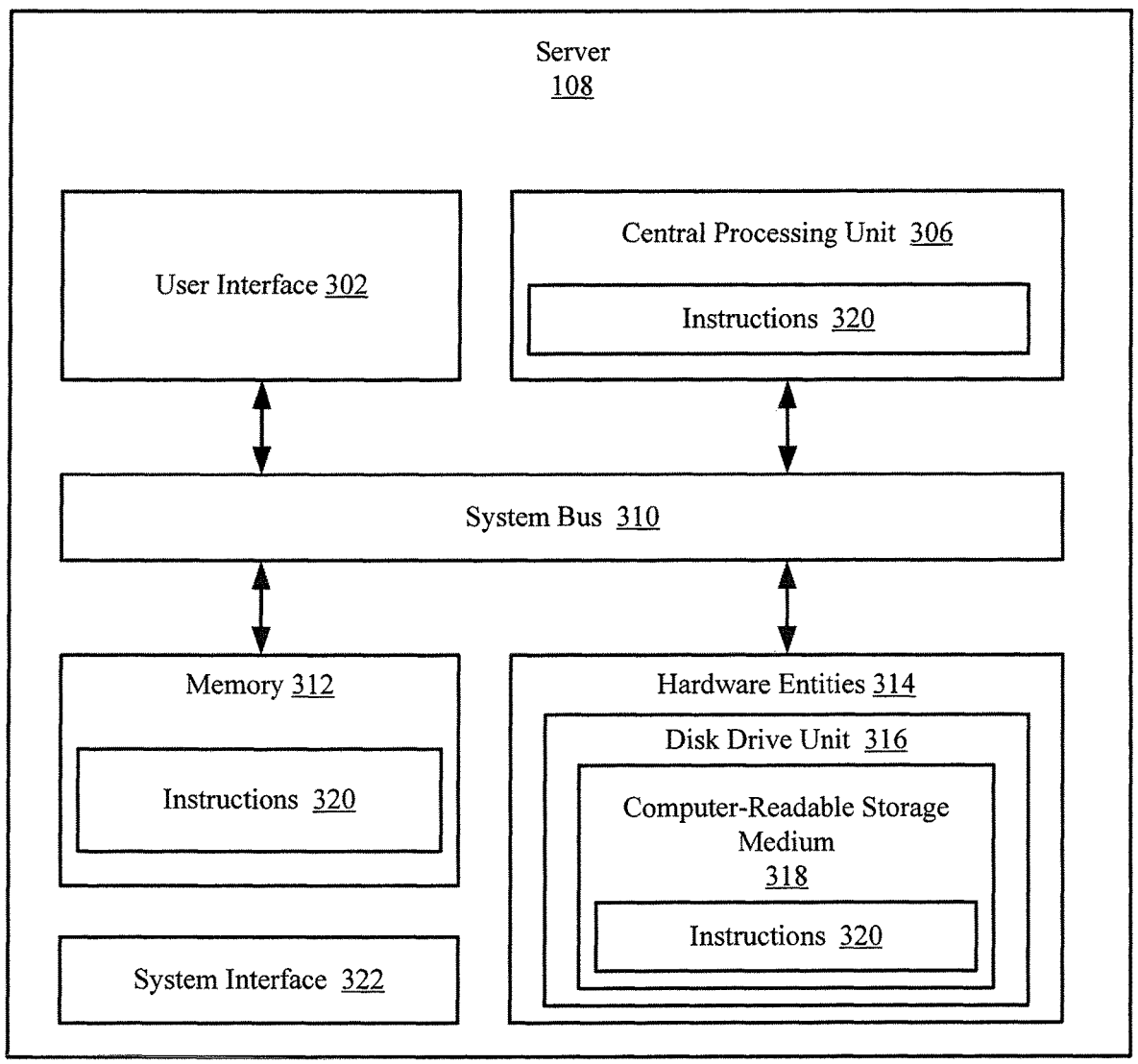
FIG. 3 is a block diagram of an exemplary server that is useful for understanding FIG. 4 provides a flow diagram of an exemplary implementation that is useful for understanding the present invention.

Referring now to FIG. 3, there is provided a more detailed block diagram of a server 106, 108, 112 of FIG. 1 that is useful for understanding the present invention. As shown in FIG. 3, the server 106, 108, 112 comprises a system interface 322, a user interface 302, a Central Processing Unit (CPU) 306, a system bus 310, a memory 312 connected to and accessible by other portions of server 108 through system bus 310, and hardware entities 314 connected to system bus 310. At least some of the hardware entities 314 perform actions involving access to and use of memory 312, which can be a Random Access Memory (RAM), a disk driver and/or a Compact Disc Read Only Memory (CD-ROM). Some or all of the listed components 302-322 can be implemented as hardware, software and/or a combination of hardware and software. The hardware includes, but is not limited to, an electronic circuit.

The server 106, 108, 112 may include more, less or different components than those illustrated in FIG. 3. However, the components shown are sufficient to disclose an illustrative embodiment implementing the present invention. The hardware architecture of FIG. 3 represents one embodiment of a representative server configured to provide supporting services to a user of a communication device (e.g., communication device 102 of FIG. 1). For example, the server 106, 108, 112 may implement a method for lookup of available auctions using an external database in communication with the server 106, 108, 112 (database not depicted), or the server may use its existing disk drive unit 316, computer-readable storage medium 318 and other facilities to store auction information, as needed. It may also provide dosage factor data to the communication device 102, as needed. Exemplary embodiments of said method will be described below in relation to FIGS. 4-5.

Hardware entities 314 can include microprocessors, Application Specific Integrated Circuits (ASICs) and other hardware. Hardware entities 314 can include a microprocessor programmed for facilitating the provision of the automatic software function control services to a user of the communication device (e.g., communication device 102 of FIG. 1). In this regard, it should be understood that the microprocessor can access and run various software applications (not shown in FIG. 3) installed on the server 106, 108, 112. Such software applications include, but are not limited to, database applications.

As shown in FIG. 3, the hardware entities 314 can include a disk drive unit 316 comprising a computer-readable storage medium 318 on which is stored one or more sets of instructions 320 (e.g., software code or code sections) configured to implement one or more of the methodologies, procedures, or functions described herein. The instructions 320 can also reside, completely or at least partially, within the memory 312 and/or within the CPU 306 during execution thereof by the server 108. The memory 312 and the CPU 306 also can constitute machine-readable media. The term "machine-readable media", as used here, refers to a single medium or multiple media (e.g., a centralized or distributed database, and/or associated caches and servers) that store the one or more sets of instructions 320. The term "machine-readable media", as used here, also refers to any medium that is capable of storing, encoding or carrying a set of instructions 320 for execution by the server 106, 108, 112 and that cause the server 106, 108, 112 to perform any one or more of the methodologies of the present disclosure.

Exemplary Methods

Figure 4:
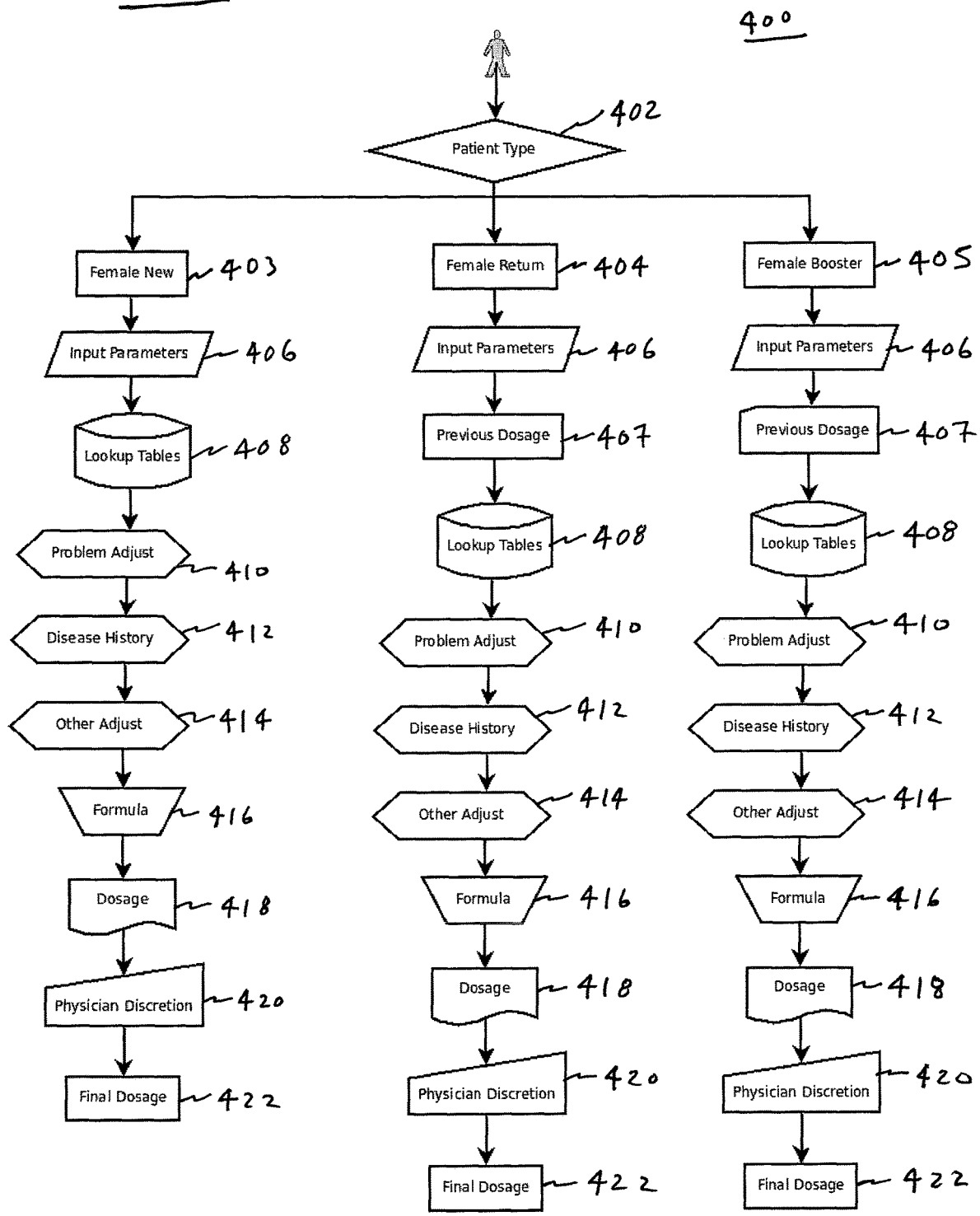
Figure 5:
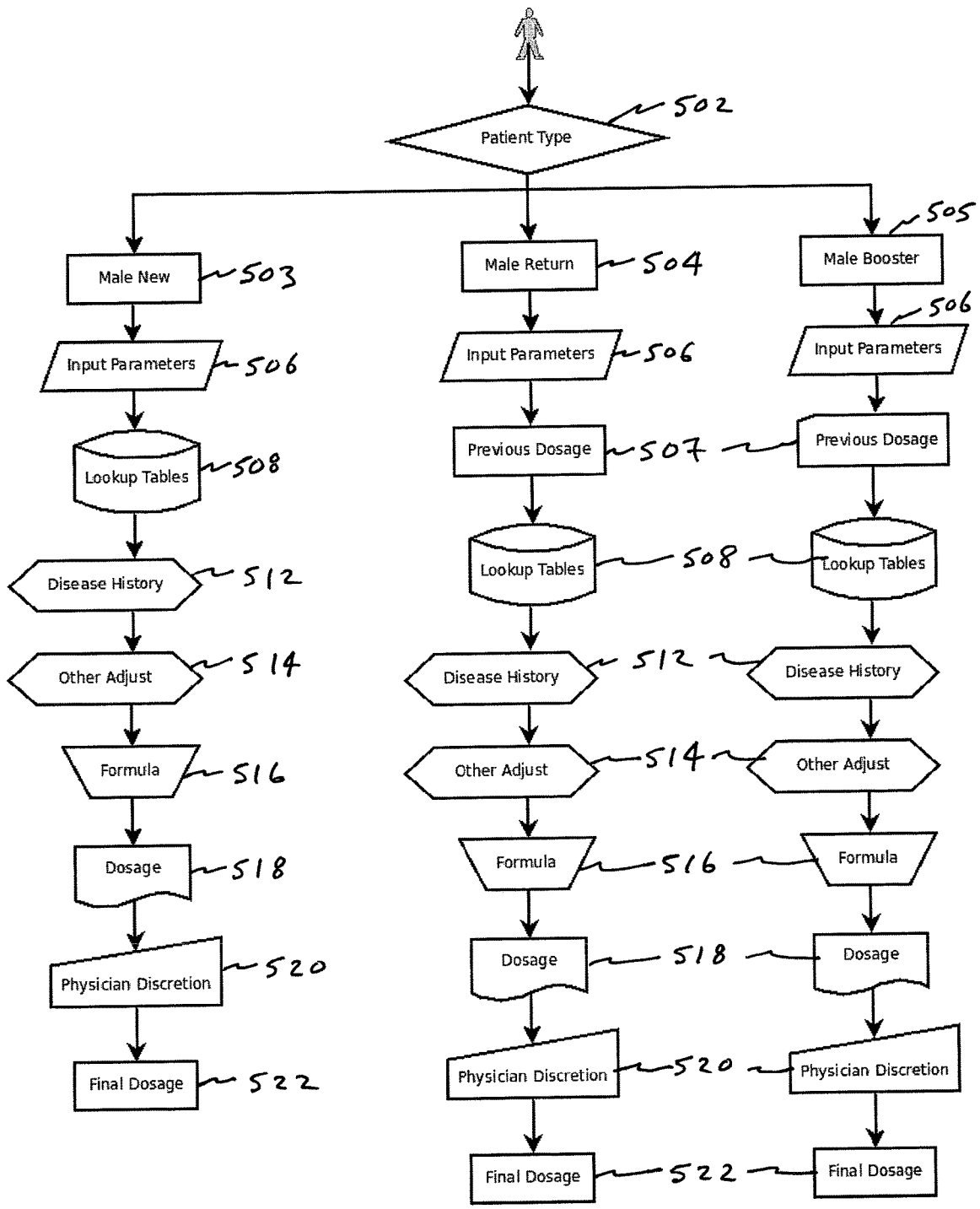
FIG. 5 provides a flow diagram of an exemplary implementation that is useful for understanding the present invention.

Referring now to FIGS. 4-5, there is provided a series of diagrams that illustrate methods for determining the most effective and safe dosage for hormone replacement therapy. Exemplary embodiments of the invention are presented in FIGS. 4-5 with respect to methods for calculating hormone replacement therapy (HR T) dosage, in particular for calculation of SOTTOPELLE™ HRT dosage. References to "HRT" in the descriptions to FIGS. 4-5 herein are understood to specifically refer to SOTTOPELLE™ HRT, unless otherwise indicated. It is understood that the tables, lookup values, factors used in these embodiments may vary depending on several variables, such as but not limited to therapy regimens, drug used, drug concentration, absorption, efficacy, and the like.

Although use of a communication device 102, as described in FIG. 2, is presented herein, the present invention is not limited in this regard. The methods are useful with alternative devices as well, such as portable computer applications, PDA applications, and tablet computing devices, and the like. The methods described in FIGS. 4-5 may be performed by an electronic circuit of the communication device 102, with the assistance of the physician 110, servers 106, 108, 112, database 114 and Internet 104, consistent with an embodiment of the invention.

As shown in FIG. 4, the method 400 begins with step 402, with the determination of patient type. FIG. 4 is generally applicable to female patients, whereas FIG. 5 is generally applicable to male patients. For exemplary purposes, the patient types are: 1. Female New Patient—A female patient that has never been treated with HR T; 2. Female Return Patient—A female patient that has been treated with HRT and is returning for ongoing treatment; 3. Female Booster Patient —A female patient that has been treated with HR T needing an additional dose prior to their next dose; 4. Male New Patient—A male patient that has never been treated with HRT; 5. Male Return Patient—A male patient that has been treated with HRT and is returning for ongoing treatment; and, 6. Male Booster Patient—A male patient that has been treated with HRT needing an additional dose prior to their next dose.

At step 402, the electronic circuit determines the patient type. In an embodiment of the invention, the physician 110 inputs the patient type directly into the communication device 102. Alternatively, the patient type may be determined from the patient name and/or a unique identification number combined with a lookup of patient information stored in a database 114.

For a Female New Patient, step 402 proceeds to 403, and then to step 406, where input parameters are input. These parameters may include patient age, height, weight, race, number of pregnancies, number of live births, number of abortions, history of renal disease, active liver disease, history of hysterectomy, history of cervical cancer, history of ovarian cancer, history of fibrocystic breast disease, history of breast cancer, current follicle stimulating hormone (FSH) level, current testosterone level, current estradiol level, current non-pellet estradiol dose, history of acne or facial hair, history of hair loss, history of PCOS, history of heavy menses and history of metabolic syndrome.

Next, at step 408, various lookup tables are consulted by the electronic circuit to determine various factors for estradiol and testosterone dosage calculation as well as dosage adjustment factors for various conditions and problems. Exemplary lookup tables used in an embodiment of the invention for female patients include Female Estradiol Weight/Age (Table 1), Female Estradiol Age (Table 2), Female Estradiol FSH (Table 3), Female Testosterone Weight (Table 4), Female Testosterone Age (Table 5), Female Testosterone Testosterone (Table 6), Conjugated Estrogen, Estradiols Pills, Estradiol Patch, Biestradiol Cream or Tabs, and Problem Factor. Exemplary tables used for HRT follow:

TABLE 1

| Female Estradiol Weight/Age | |
| --- | --- |
| Weight/Age Ratio (lbs/Years) | Lookup Value (mg) |
| 0-1.5 | 1 |
| 1.6-2.5 | 2 |
| 2.6-3.9 | 3 |
| >4 | 2 |

TABLE 2

| Female Estradiol Age | |
| --- | --- |
| Age (Years) | Lookup Value |
| <40 | 3 |
| 40-50 | 5 |
| 51-60 | 15 |
| 61-68 | 12.5 |
| >68 | 4 |

TABLE 3

| Female Estradiol FSH | |
| --- | --- |
| FSH | Lookup Value |
| <31 | 0 |
| 31-50 | 1 |
| 51-100 | 2 |
| >100 | 3 |

TABLE 4

| Female Testosterone Weight | |
| --- | --- |
| Weight (lbs.) | Lookup Value (mg) |
| 75-150 | 75 |
| 151-200 | 87.5 |
| >200 | 100 |

TABLE 5

| Female Testosterone Age | |
| --- | --- |
| Age (Years) | Lookup Value |
| 0-67 | 1 |
| >67 | 0.63 |

TABLE 6

| Female testosterone Testosterone | |
| --- | --- |
| Testosterone | Lookup Value (mg) |
| 0-20 | 37.5 |
| 21-100 | 25 |
| >100 | 0 |

After obtaining the lookup values from the various tables in step 408, additional problem adjustment factors are determined in step 410, disease history is factored in step 412, and other adjustments are determined in step 414. In an embodiment of the invention, these various considerations may include, but are not limited to: Female Estradiol Problem Factor, Conjugated Estrogen, Estradiols Pills, Estradiol Patch, Biestradiol Cream or Tabs, and Problem Factor. Exemplary adjustment factors applied to the dosage determined after application of the lookup values to the base dosage, i.e., "test dosage" may include, but are not limited to: for history of acne or facial hair, dosage=test dosage× 0.90; history of hair loss, dosage=test dosage×0.88; hysterectomy, if YES, dosage=test dosage×0.88; history of PCOS, dosage=test dosage×0.75; history of heavy menses, if YES, dosage=test dosage×0.88; history of metabolic syndrome, if YES, DO NOTHING; persistent breast pain, if YES, dosage=test dosage×0.80; mid-cycle bleeding, if YES, dosage=test dosage×0.80; headache, if YES, dosage=test dosage×0.75; fluid retention, if YES, dosage=test dosage× 0.75; and, fibrocystic breast disease, if YES, dosage=test dosage×0.70. Also, if the FSH is >=30 and age is between 20 and 50 years, then the FSH adjustment lookup value is set to 12.5.

Next, at step 416, formula are applied to determine female dosage for estradiol and testosterone. Female dosage calculations involve two calculations, one for extradiol and the other for testosterone. The estradiol calculation involves calculating the weight/age ratio, age, current FSH levels, a problem factor multiplier and an FSH adjustment factor. The weight/age ratio is calculated by dividing the weight in lbs. by the age in years. As indicated above, the weight/age ratio is then used to lookup the weight/age ratio lookup value from Table 1. The age is then used to lookup the lookup value in the Female Estradiol Age lookup table (Table 2). The value of the current FSH level is then used to find the corresponding lookup value in the Female Estradiol FSH lookup table (Table 3). These values are then summed into a single value and then multiplied by any problem factor adjustment values, and added to the calculation. The estradiol dosage is thus calculated as:

Estradiol dosage=((Weight Age Ratio Lookup+Age Lookup+FSH Lookup)×Problem Factor)+FSH Adjustment Similarly, the testosterone calculation involves calculating the weight lookup value, current testosterone level lookup value and testosterone age lookup value. The weight is used to obtain a value from the Female Testosterone Weight lookup table (Table 4). The current testosterone level is used to obtain a value in the Female Testosterone Testosterone lookup table (Table 5). These two values are then summed. The age is used to obtain a value in the Female Testosterone Age lookup table (Table 6). The obtained testosterone age lookup value is then multiplied by the sum of the testosterone weight and testosterone testosterone lookup values. The testosterone dosage is thus calculated as:

Testosterone dosage=(Weight Testosterone Lookup+ Testosterone Level Lookup)×Testosterone Age Lookup Exception logic applies at step 420 at the physician's discretion for premenopausal women: pre-menopausal females do not get estradiol except in the case where current estradiol level is <10 or if they exhibit symptoms of migraines. For pre-menopausal women without estradiol level<10 or migraines, estradiol calculated dose becomes 0.00. The process is complete at step 422, with final dosage determination.

Like the dosage calculations for female new patients, female return dosage calculations also involve two components: one for estradiol and the other for testosterone. The method includes all the steps included for a new patient, and also step 407 interposed immediately after step 406. In step 407, the patient's previous dosage of estradiol is determined. This previous dosage may be directly input or may be saved in a database. The female return patient estradiol dosage is then calculated at step 416 using the following formula:

Estradiol dosage=((Weight Age Lookup+Age Lookup+FSH Lookup+Current Dose Lookup)× Problem Factor)

Female Return Testosterone dosage is calculated using the following formula:

Testosterone dosage=(Weight Testosterone Lookup+ Testosterone Level Lookup)×Testosterone Age Lookup Calculation of female booster dosages for estradiol and testosterone is determined in step 416, respectively, by taking the previous estradiol dosage and dividing by 2.00, and taking the previous testosterone dosage and dividing by 3.00.

Referring now to FIG. 5, methods of determining dosage for male patients is presented. At step 502, the electronic circuit determines the patient type. In an embodiment of the invention, the physician 110 inputs the patient type directly into the communication device 102. Alternatively, the patient type may be determined from the patient name and/or a unique identification number combined with a lookup of patient information stored in a database 114.

For a Male New Patient, step 502 proceeds to 503, and then to step 506, where input parameters are input. These parameters may include patient age, height, weight, race, history of hypertension, history of diabetes, history of colon cancer, history of testicular cancer, history of BPH, history of prostate cancer, history of renal disease, active liver disease and current testosterone level. Next, at step 508, various lookup tables are consulted to determine a base dosage for testosterone and adjustment factors for various conditions and problems. Exemplary lookup tables used in an embodiment of the invention for male patients include Male Age and Male Weight, Exemplary tables used for HRT follow:

TABLE 7

| Male Age | |
| --- | --- |
| Age (Years) | Lookup Value |
| <69 | 1 |
| >68 | 0.8 |

TABLE 8

| Male Weight | |
| --- | --- |
| Weight (lbs.) | Lookup Value (mg) |
| <151 | 1200 |
| 151-175 | 1400 |
| 176-200 | 1600 |
| 201-225 | 1800 |
| 226-250 | 2000 |
| 251-275 | 2200 |
| 276-300 | 2400 |
| 301-350 | 2600 |
| 351-400 | 2800 |
| >400 | 3000 |

After obtaining the lookup values from the various tables in step 508, additional problem adjustment factors are determined in step 510, disease history is factored in step 512, and other adjustments are determined in step 514. In an embodiment of the invention, these various considerations may include, but are not limited to: Diabetes and Metabolic Syndrome. In the case of Diabetes or Metabolic Syndrome, the testosterone dosage is increased by 100 mg. Exemplary adjustment factors applied to the dosage determined after application of the lookup values to the base dosage, i.e., "test dosage" may include, but are not limited to: for history of BPH, dosage=test dosage×0.95; history of prostate cancer, dosage=test dosage×0.90; history of both prostate cancer and BPH, dosage=test dosage×0.90; physical activity level: sedentary/work only, decrease dosage by 100 mg, work+ exercise 5 times/week, increase dosage by 100 mg; testosterone level>=700, no treatment; monthly testosterone injection (100-200 mg), no change in dosage; weekly testosterone injection (100-200 mg), increase dosage by 100 mg; testosterone gel (1.62%) used, increase dosage by 100 mg.

Next, at step 516, formula are applied to determine male dosage for testosterone HRT. Male dosage calculations involve a single calculation for testosterone. The testosterone calculation involves calculating the weight lookup value, age lookup value, obtaining the current testosterone dose value, if any, and applying any additional adjustments (from above). As indicated above, the age is used to lookup the age lookup value from Table 7. The weight is then used to lookup the lookup value in the Male Weight lookup table (Table 8). These values are then multiplied together with the applicable adjustment factor to determine the testosterone dosage. The testosterone dosage is thus calculated as:

Testosterone dosage=Age Testosterone Lookup× Weight Testosterone Lookup×other Adjustment Multiplication Factor Dosage calculations for male return patients are provided m step 507 by application of the following formula:

If Current Testosterone Dosage<400.00 mg,then

Return Testosterone dosage=previous Testosterone Dosage+200.00 mg;

Else

Return Testosterone dosage=previous Testosterone Dosage

Male booster testosterone dosage is dependent on existing or previous historical conditions such as BPH, cancer or combinations thereof, as included in the adjustment factor calculated for male new patients, above. The booster testosterone dosage is then determined as:

Booster testosterone dosage=previous testosterone dosage+(0.20×adjustment Multiplication Factor)

All of the apparatus, methods and algorithms disclosed and claimed herein can be made and executed without undue experimentation in light of the present disclosure. While the invention has been described in terms of preferred embodiments, it will be apparent to those of skill in the art that variations may be applied to the apparatus, methods and sequence of steps of the methods without departing from the concept, spirit and scope of the invention. More specifically, it will be apparent that certain components may be added to, combined with, or substituted for the components described herein while the same or similar results would be achieved. All such similar substitutes and modifications apparent to those skilled in the art are deemed to be within the spirit, scope and concept of the invention as defined.

What is claimed is:

1. A method of treating a patient with hormone replacement therapy,
the method comprising:
  receiving, by a user interface of a computerized device, an input indicating a patient gender and transmitting the patient gender input to a processor of the computerized device;
  receiving, by the processor, a current level of testosterone for the patient;
  receiving, by the processor, a current level of estradiol treatment for the patient;
  assigning, by the processor, a male testosterone dosage in response to receiving a patient gender input that is male using a process comprising:
    receiving, by the processor, an input indicating a patient weight;
    accessing, by the processor, a lookup table comprising a base testosterone dosage and determining, by the processor, the base testosterone dosage based on the patient weight;
    determining, by the processor, a first intermediate testosterone dosage by multiplying the base testosterone dosage by a male age factor;
    determining, by the processor, a second intermediate testosterone dosage by multiplying the first intermediate testosterone dosage by a male adjustment factor based on a received input of a patient history of prostate cancer or benign prostatic hyperplasia (BPH;
    determining, by the processor, the male testosterone treatment dosage by adding a male increment based on a received input of a level of physical activity;
    if the current level of testosterone is below 700 mg, assigning the male testosterone dosage to the male patient; and
  administering the assigned male testosterone dosage to the male patient; and
  assigning, by the processor, an estradiol dosage in response to receiving a patient gender input that is female using a process comprising:
    receiving, by the processor, an input comprising a patient weight and an input comprising a patient age;
    receiving, by the processor, a current level of follicle stimulating hormone (FSH) for the patient;
    accessing, by the processor, a first lookup table comprising a first base estradiol dosage and determining, by the processor, the first base estroidiol dosage based on a ratio of the patient weight to the patient age;
    accessing, by the processor, a second lookup table comprising a second base estradiol dosage and determining, by the processor, the second base estradiol dosage based on the patient age;
    accessing, by the processor, a third lookup table comprising a third base estradiol dosage and determining, by the processor, the third base estradiol dosage based on a received input of the current level of follicle stimulating hormone (FSH) of the patient;
    determining, by the processor, a first intermediate estradiol dosage by summing the first, second, and third base estradiol dosages;
    determining, by the processor, a second intermediate estradiol dosage by multiplying the first intermediate estradiol dosage by a problem factor;
    determining, by the processor, the estradiol dosage by adding an FSH adjustment to the second intermediate estradiol dosage; and
    assigning, by the processor, the estradiol dosage if the patient is not premenopausal; and
  assigning, by the processor, a testosterone dosage in response to receiving a patient gender input that is female using a process comprising:
    accessing, by the processor, a fourth lookup table comprising a first base testosterone dosage and determining, by the processor, a first base testosterone dosage based on the patient weight;

accessing, by the processor, a fifth lookup table comprising a second base testosterone dosage and determining, by the processor, a second base testosterone dosage based on a received input of a current level of testosterone of the patient;

determining, by the processor, the female testosterone dosage by summing the first and second base testosterone dosages and multiplying by a female age factor;

assigning, by the processor, the female testosterone dosage to the female patient; and administering at least one of the female estradiol dosage and the female testosterone dosage to the female patient.

2. The method of claim 1, wherein the base testosterone dosage is based on weight according to the following table:

| Weight (lbs.) | Value (mg) |
|---|---|
| <151 | 1200 |
| 151-175 | 1400 |
| 176-200 | 1600 |
| 201-225 | 1800 |
| 226-250 | 2000 |
| 251-275 | 2200 |
| 276-300 | 2400 |
| 301-350 | 2600 |
| 351-400 | 2800 |
| >400 | 3000. |

3. The method of claim 2, wherein the male adjustment factor is 0.95 if the patient has a history of BPH, 0.90 if the patient has a history of prostate cancer, and 0.90 if the patient has a history of both BPH and prostate cancer.

4. The method of claim 3, wherein the male increment is −100 mg if the patient is sedentary, +100 mg if the patient exercises 5 times/week, receives a weekly testosterone injection, or uses a testosterone gel.

5. The method of claim 1, wherein the first base estradiol dosage is based on a ratio of weight to age according to the following table:

| Weight/Age Ratio (lbs/Years) | Value (mg) |
|---|---|
| 0-1.5 | 1 |
| 1.6-2.5 | 2 |
| 2.6-3.9 | 3 |
| >4 | 2. |

6. The method of claim 5, wherein the second base estradiol dosage is based on age according to the following table:

| Age (Years) | Value |
|---|---|
| <40 | 3 |
| 40-50 | 5 |
| 51-60 | 15 |
| 61-68 | 12.5 |
| >68 | 4. |

7. The method of claim 6, wherein the third base estradiol dosage is based on the current level of FSH according to the following table:

| FSH | Value |
|---|---|
| <31 | 0 |
| 31-50 | 1 |
| 51-100 | 2 |
| >100 | 3. |

8. The method of claim 7, wherein the problem factor is 0.90 if the patient has a history of acne or facial hair, 0.88 if the patient has a history of hair loss or heavy menses or has had a hysterectomy, 0.80 if the patient has a history of persistent breast pain or mid-cycle bleeding, 0.75 if the patient has a history of PCOS, headache, or fluid retention, and 0.70 if the patient has a history of fibrocystic breast disease.

9. The method of claim 8, wherein the FSH adjustment factor is 12.5 if the patient is between 20 and 50 years of age and the FSH is 30 or more.

10. The method of claim 1, wherein the first base testosterone dosage is based on weight according to the following table:

| Weight (lbs) | Value (mg) |
|---|---|
| 75-150 | 75 |
| 151-200 | 87.5 |
| >200 | 100. |

11. The method of claim 10, wherein the female age factor is based on age according to the following table:

| Age (Years) | Value |
|---|---|
| 0-67 | 1 |
| >67 | 0.63. |

12. A method of treating a patient with hormone replacement therapy, comprising:

receiving, by a processor of a computerized device, an input of a current level of testosterone for a hormone replacement therapy patient;

receiving, by the processor, an input of a current level of testosterone treatment for the patient;

receiving, by the processor, an input of a current level of estradiol treatment for the patient;

if the patient is male, assigning a male testosterone dosage by a process comprising:

determining, by the processor, a base testosterone dosage based on a received input of a weight of the patient;

receiving, by the processor an input of an age of the patient;

determining, by the processor, a first intermediate testosterone dosage by multiplying the base testosterone dosage by 0.80 if the patient is above 68 years of age;

determining, by the processor, a second intermediate testosterone dosage by multiplying the first intermediate testosterone dosage by a male adjustment factor based on history of prostate cancer or benign prostatic hyperplasia (BPH;

determining, by the processor, the male testosterone dosage by adding a male increment based on level of physical activity;

assigning, by the processor, the male testosterone dosage; and administering the assigned male testosterone dosage to the male patient;

if the patient is female, assigning an estradiol dosage by a process comprising:

receiving, by the processor, an input of a current level of follicle stimulating hormone (FSH), a weight, and an age for the patient;

determining, by the processor, a first base estradiol dosage based on a ratio of weight to age;

determining, by the processor, a second base estradiol dosage based on the age of the patient according to the following table:

| Age (Years) | Value |
|---|---|
| <40 | 3 |
| 40-50 | 5 |
| 51-60 | 15 |
| 61-68 | 12.5 |
| >68 | 4; | determining, by the processor, a third base estradiol dosage based on the current level of FSH;

determining, by the processor, a first intermediate estradiol dosage by summing the first, second, and third base estradiol dosages;

determining, by the processor, a second intermediate estradiol dosage by multiplying the first intermediate estradiol dosage by a problem factor;

determining, by the processor, the estradiol dosage by adding an FSH adjustment to the second intermediate estradiol dosage; and assigning, by the processor, the estradiol dosage if the patient is not premenopausal;

and if the patient is female, assigning a female testosterone dosage by a process comprising:

determining, by the processor, a first base testosterone dosage based on weight;

determining, by the processor, a second base testosterone dosage based on a received input of a current level of testosterone;

determining, by the processor, the female testosterone dosage by summing the first and second base testosterone dosages and multiplying by a female age factor;

assigning the female testosterone dosage; and administering at least one of the assigned female estradiol dosage and assigned female testosterone dosage to the female patient.

13. The method of claim 12, wherein the base testosterone dosage is based on weight according to the following table:

| Weight (lbs.) | Value (mg) |
|---|---|
| <151 | 1200 |
| 151-175 | 1400 |
| 176-200 | 1600 |
| 201-225 | 1800 |
| 226-250 | 2000 |
| 251-275 | 2200 |
| 276-300 | 2400 |
| 301-350 | 2600 |
| 351-400 | 2800 |
| >400 | 3000. |

14. The method of claim 13, wherein the male adjustment factor is 0.95 if the patient has a history of BPH, 0.90 if the patient has a history of prostate cancer, and 0.90 if the patient has a history of both BPH and prostate cancer.

15. The method of claim 14, wherein the male increment is −100 mg if the patient is sedentary, +100 mg if the patient exercises 5 times/week, receives a weekly testosterone injection, or uses a testosterone gel.

16. The method of claim 12, wherein the first base estradiol dosage is based on a ratio of weight to age according to the following table:

| Weight/Age Ratio (lbs/Years) | Value (mg) |
|---|---|
| 0-1.5 | 1 |
| 1.6-2.5 | 2 |
| 2.6-3.9 | 3 |
| >4 | 2. |

17. The method of claim 16, wherein the third base estradiol dosage is based on the current level of FSH according to the following table:

| FSH | Value |
|---|---|
| <31 | 0 |
| 31-50 | 1 |
| 51-100 | 2 |
| >100 | 3. |

18. The method of claim 17, wherein the problem factor is 0.90 if the patient has a history of acne or facial hair, 0.88 if the patient has a history of hair loss or heavy menses or has had a hysterectomy, 0.80 if the patient has a history of persistent breast pain or mid-cycle bleeding, 0.75 if the patient has a history of PCOS, headache, or fluid retention, and 0.70 if the patient has a history of fibrocystic breast disease.

19. The method of claim 18, wherein the FSH adjustment factor is 12.5 if the patient is between 20 and 50 years of age and the FSH is 30 or more.

20. The method of claim 12, wherein the first base testosterone dosage is based on weight according to the following table:

| Weight (lbs) | Value (mg) |
|---|---|
| 75-150 | 75 |
| 151-200 | 87.5 |
| >200 | 100. |

* * * * *